(12) United States Patent
Whittlesey et al.

(10) Patent No.: US 7,310,895 B2
(45) Date of Patent: Dec. 25, 2007

(54) SHOE WITH SENSORS, CONTROLLER AND ACTIVE-RESPONSE ELEMENTS AND METHOD FOR USE THEREOF

(75) Inventors: Saunders N Whittlesey, Deerfield, MA (US); Douglas K Robinson, Mansfield, MA (US); John J Erickson, Brockton, MA (US)

(73) Assignee: Acushnet Company, Fairhaven, MA (US)

( * ) Notice: Subject to any disclaimer, the term of this patent is extended or adjusted under 35 U.S.C. 154(b) by 429 days.

(21) Appl. No.: 10/790,164

(22) Filed: Mar. 1, 2004

(65) Prior Publication Data

US 2005/0188566 A1  Sep. 1, 2005

(51) Int. Cl.
*A43B 5/00* (2006.01)
(52) U.S. Cl. .......................... 36/137; 36/50.1; 36/25 R; 73/172; 73/179
(58) Field of Classification Search .................. 36/137, 36/50.1, 29, 25 R, 54; 73/172, 179
See application file for complete search history.

(56) References Cited

U.S. PATENT DOCUMENTS

| | | | |
|---|---|---|---|
| 3,974,491 A | 8/1976 | Sipe ........................... | 340/272 |
| 4,814,661 A | 3/1989 | Ratzlaff et al. ............. | 310/328 |
| 5,230,249 A * | 7/1993 | Sasaki et al. .................. | 36/29 |
| 5,437,289 A * | 8/1995 | Liverance et al. ............ | 36/136 |
| 5,500,635 A * | 3/1996 | Mott ........................... | 33/3 A |
| 5,642,096 A * | 6/1997 | Leyerer et al. ............... | 73/172 |
| 5,813,142 A * | 9/1998 | Demon ......................... | 36/29 |
| 5,839,210 A | 11/1998 | Bernier et al. ............... | 36/50.1 |
| 5,918,502 A * | 7/1999 | Bishop ........................ | 73/172 |
| 6,001,023 A | 12/1999 | Sanchez et al. ............. | 473/217 |
| 6,032,387 A | 3/2000 | Johnson ....................... | 36/50.1 |
| 6,059,674 A | 5/2000 | Umlauft ...................... | 473/537 |
| 6,106,417 A | 8/2000 | Umlauft et al. ............. | 473/537 |
| 6,433,465 B1 | 8/2002 | McKnight et al. .......... | 310/339 |
| 6,474,003 B2 | 11/2002 | Erickson et al. ............. | 36/100 |
| 6,545,384 B1 | 4/2003 | Pelrine et al. .............. | 310/309 |
| 6,598,322 B2 | 7/2003 | Jacques et al. .............. | 36/50.1 |
| 6,604,419 B2 * | 8/2003 | Guzman ....................... | 36/132 |
| 6,616,544 B2 | 9/2003 | Kimmorley .................. | 473/218 |
| 6,865,825 B2 * | 3/2005 | Bailey et al. ................... | 36/29 |
| 2003/0070324 A1 * | 4/2003 | Nelson ........................ | 36/137 |
| 2004/0103563 A1 * | 6/2004 | Linge ........................... | 36/137 |
| 2004/0177531 A1 * | 9/2004 | DiBenedetto et al. ......... | 36/132 |
| 2007/0006489 A1 | 1/2007 | Case, Jr. et al. | |

\* cited by examiner

*Primary Examiner*—Marie Patterson
(74) *Attorney, Agent, or Firm*—Kristin D. Wheeler

(57) ABSTRACT

Active-response golf shoes are disclosed. The golf shoes include at least one sensor, a controller, and at least one active-response element. The sensor and controller operate to rapidly determine if a golfer is walking or swinging a golf club. Once this determination is made the controller and active-response element rapidly change the shoe's characteristics. If the controller determines that the golfer is walking, the shoe provides a soft and flexible walking platform. If the controller determines that the golfer is swinging, the shoe morphs or changes automatically to provide a stable hitting platform. The controller senses various predetermined conditions such as pressure under the ball of the user's foot to determine whether the golfer is walking or swinging. The active-response elements may be a sole adjuster, a lace adjuster, and/or an upper adjuster. Methods of determining the golfer's type of movement are also disclosed.

28 Claims, 4 Drawing Sheets

SHOE WITH SENSORS, CONTROLLER AND ACTIVE-RESPONSE ELEMENTS AND METHOD FOR USE THEREOF

FIELD OF THE INVENTION

The present invention relates to shoes, and more particularly, to golf shoes having sensors, controller, and active-response elements. In addition, the present invention relates to a method for actuating the active-response elements and changing the shoe's characteristics depending on whether the player is walking or swinging their clubs.

BACKGROUND OF THE INVENTION

The game of golf includes long stretches of walking and short moments of swinging a golf club to hit a golf ball. Consequently, golf shoes must perform in two different types of movement that have conflicting design requirements. Golf shoes generally include an upper joined to a sole assembly. The sole assembly includes an outsole that contacts the ground. When walking, it is most desirable for the upper and outsole to be soft and flexible so that a golfer's feet are comfortably supported. The upper is more flexible when the laces in the upper are loosely tied. The outsole is soft and flexible by selecting a material with these characteristics and defining flex grooves and notches in the outsole.

When swinging a golf club, great forces are created that may make a golfer's foot move relative to the outsole or make the outsole move relative to the ground. To counteract this tendency, it is desirable for the upper and outsole to be non-deformable and stable. When the laces in the shoe upper are tightly tensioned to tighten the upper, foot movement in the shoe is reduced. The outsole is more stable when made with a rigid material. Thus, the conflict in design requirements is clearly defined.

There have been a number of other proposed solutions to this conundrum. One is for golfers to change shoes between walking and swinging. This solution is undesirable since it would require too much time and effort on the golfer's part. Alternatively, the golfer could adjust their laces between swings, e.g., tightening the laces for swinging and loosening them for walking. This solution is also undesirable because it would also require significant effort from the golfer. Most manufacturers compromise between walking and swinging requirements when making their golf shoes, so that the shoe operates well during both walking and swinging. For example, commonly owned U.S. Pat. No. 6,474,003 to Erickson and Robinson discloses golf shoes having a footbed system with variable sized heel cups.

Another approach is suggested in U.S. Pat. No. 6,598,322 to Jacques. This patent discloses shoes with at least one elongated shape memory alloy element forming laces and an electric circuit. When the circuit is energized, the shape memory alloy shortens and tightens the shoe upper around the foot of a wearer. The circuit is energized by a switch in the heel of the shoe that is turned on by the golfer clicking the heels together. This is not ideal, as it requires the golfer to perform an additional "clicking" action not normally performed when playing golf. An additional abnormal action may interfere with the golfer's performance. This action may also subject the golfer to ridicule. Alternatively, U.S. Pat. No. 6,032,387 to Johnson discloses a shoe with a mechanical tightening and loosening apparatus, which must be manually actuated. Similarly, U.S. Pat. No. 5,839,210 to Bernier et al. discloses a shoe with a shoe tightening apparatus that is also manually actuated.

Performance enhancing footwear is disclosed in U.S. Pat. No. 5,918,502 to Bishop. This patent discloses footwear with a piezoelectric spring apparatus in the sole. Walking or running applies a first force that deforms the spring and generates electrical energy, which is stored in a circuit. When a second force greater than the first force is sensed, such as when a wearer is preparing to jump, the stored energy is released which deforms the spring and imparts a force into the bottom of the sole to assist in the jumping action. This footwear does not address the game of golf and the functional requirements of a golf shoe. Moreover, USGA rules prohibit using shoes with stored energy.

Other sporting devices, such as tennis and racquetball racquets incorporate piezoelectric ceramic fibers to alter their mechanical properties, as disclosed in U.S. Pat Nos. 6,059,674 and 6,106,417. These racquets dampen the vibrations propagating from the hitting surface toward the handle. When the piezoelectric fibers deform, they produce an electrical charge, and vice versa, when a voltage is applied to the piezoelectric fibers, they deform. When a ball impacts the racquet's strings, the impact creates about 50V of voltage from the piezoelectric fibers positioned near the racquet's hitting surface. This discharge is received by an interface circuit in the handle that amplifies the discharge about 7 times and that feeds the discharge back about 5 ms later. This amplified discharge can deflect the racquet up to 1 mm. The vibration caused by the impact is thus reduced up to about 50%. Hence, the vibration created by the impact is received by the circuit, and is amplified and returned with a phase shift to counter the vibrations.

This concept was also applied to skis, where piezoelectric fibers are positioned at about 45° angle to the longitudinal axis of the skis. In one example, an 800V excitation applied to these fibers can twist the skis about 1 cm. These racquets and skis are self-powered and require no battery.

Hence, there remains a need in the art for golf shoes that optimally meet the walking and swinging design requirements without the golfer having to perform any additional actions.

SUMMARY OF THE INVENTION

Accordingly, the present invention provides golf shoes that distinguish between walking and swinging a golf club.

The invention also provides golf shoes exhibiting a first set of characteristics when the wearer is walking and a second set of characteristics when the wearer is swinging. The first set of characteristics is indicative of a soft/flexible shoe, and the second set of characteristics is indicative of a stable shoe.

The present invention is directed to a shoe comprising an upper, at least one active-response element, a sole coupled to the upper to define a chamber for receiving a wearer's foot and a controller operatively connected to the sensor and active-response element. The sole includes at least one sensor. The controller determines whether the wearer is walking or swinging and when the wearer is swinging. When the wearer is swinging, the controller sends an output current to the active-response element and the active-response element changes the shoe from an initial state where the shoe exhibits a first set of characteristics to a transitory state where the shoe exhibits a second set of characteristics different from said first set of characteristics.

Alternatively, said output current is sent to said sensor, and said sensor sends said output current to said active-response element. The active-response element comprises a sole adjuster, an upper adjuster, a tongue adjuster or a lace adjuster.

The first set of characteristics is indicative of walking, and the second set of characteristics is indicative of swinging. While walking, the energy generated by the sensor is harvested. While swinging, the controller converts the harvested energy to the output current. The shoe is more stable for swinging the club when it exhibits the second set of characteristics than the first set of characteristics, and when the shoe is more stable the wearer's foot is less movable relative to the shoe.

The controller sends said output current if said sensor senses a change pressure greater than a preset swing threshold within a preset time interval threshold. The swing threshold is between about 70 kPa to about 140 kPa, and preferably about 100 kPa, and the time interval threshold is about 0.5 second.

In another embodiment, the sole comprises at least two sensors, wherein the two sensors are located proximately under any two metatarsal heads. The two sensors are spaced apart, and preferably one sensor is located under the fourth metatarsal bone and another sensor is located under the fifth metatarsal bone. When the wearer is walking, the at least two sensors sense pressure peaks at about the same time. When the wearer is swinging, the at least two sensors sense pressure peaks sequentially.

Methods of determining whether the wearer is walking or swinging and to change the shoe's characteristics from walking to swing are also disclosed.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE INVENTION

Figure 1:
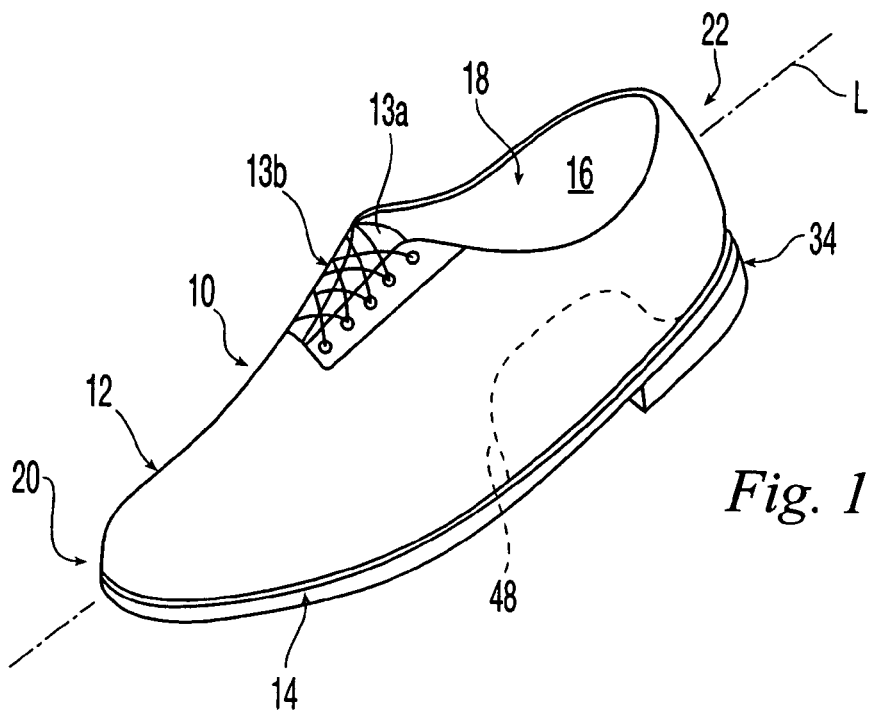
FIG. 1 is a lateral side, perspective view of a preferred embodiment of a golf shoe of the present invention.

Referring to FIG. 1, there is illustrated an embodiment of a golf shoe 10 in accordance to the present invention. Either or both right or left shoes could utilize the features of the present invention. The shoe 10 includes an upper 12 and a sole assembly 14. The upper is joined to the sole assembly 14 using cement, stitching or other conventional materials and conventional techniques. Once joined, the upper 12 defines a chamber 16 for receiving a wearer's foot (not shown). The chamber 16 is accessible by an opening 18 in the upper 12.

Figure 2:
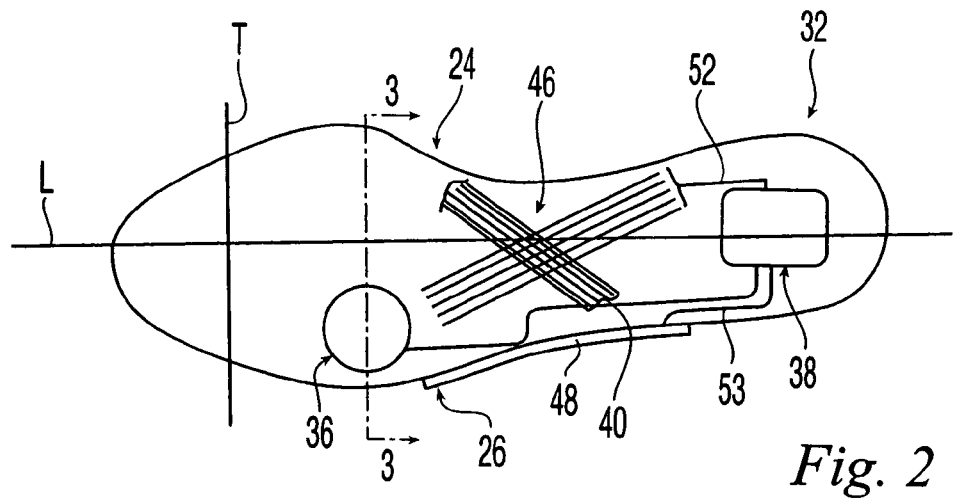
FIG. 2 is a schematic, plan view showing various sensors, a controller, and active-response elements within an outsole of the shoe of FIG. 1.

For reference purposes, golf shoe 10 includes a front or toe end 20, a rear or heel end 22, and a longitudinal axis L extending between the front end 20 and the rear end 22. Referring to FIGS. 1 and 2, the golf shoe 10 further includes a medial side 24 and a lateral side 26. A transverse axis T perpendicular to the longitudinal axis L extends between the medial side 24 and lateral side 26. When golfers walk, their feet typically move along the longitudinal axis L. When golfers swing, their feet typically move along the transverse axis T.

The upper 12 is preferably formed of one or multiple layers of conventional materials, such as leather, synthetic materials or combinations of these. The materials are cut and then stitched together over a foot-shaped last to form the finished upper 12, as known by those of ordinary skill in the art. The upper 12 preferably includes a tongue 13a and laces 13b that allow the opening 18 to be enlarged to allow the wearer's foot to be inserted in the shoe. Increasing the tension on the laces 13b reduces the opening 18 and tightens the upper 12 about the wearer's foot.

Figure 3:
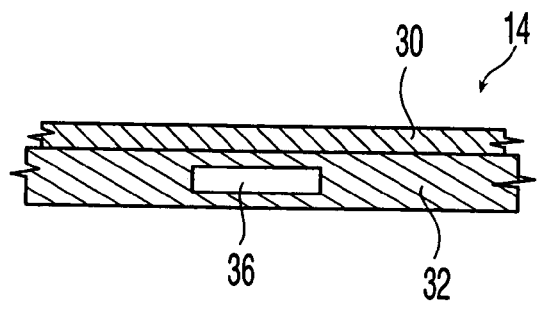
FIG. 3 is a cross-sectional view showing one sensor within the outsole taken along line 3-3 of FIG. 2.

Referring to FIGS. 1-3, the sole assembly 14 includes an optional midsole 30 and an outsole 32. The midsole 30 provides cushioning to the wearer and the outsole provides lateral or transverse stability, longitudinal flexibility, and durability so that it can withstand repeated contact with the ground. Additionally, the sole assembly 14 may include other components such as a stiff board, other cushions, etc.

The midsole 30 may be formed of conventional materials such as rubber or an ethylene vinyl acetate copolymer (EVA). Once the midsole 30 and outsole 32 are joined, the midsole 30 forms the interior, upward facing surface of the sole assembly 14 that is contacted by the wearer's foot. On the other hand, the outsole 32 forms the bottom surface of the sole that contacts the ground, except for a heel section 34.

Outsole 32 may be formed of various conventional materials such as leather or various synthetic materials, such as thermoplastics. In such an embodiment, the outsole may further include metal or plastic which can be fixed or removable. Alternatively, the outsole 32 may be formed of all thermoplastic materials with integral projections for traction for a so-called "spikeless" outsole.

With reference to FIG. 2, the outsole 32 includes a pressure sensor 36 and a controller 38 electrically connected by a conductive wire 40. In the present embodiment with reference to FIG. 3, the pressure sensor 36 is molded within the outsole 32. Sensor 36 can also be located in midsole 30 or in upper 12.

Preferably, the pressure sensor 36 is located so that it underlies the ball of a wearer's foot. More preferably, the pressure sensor 36 is located so that it underlies the lateral side of the ball of the wearer's foot. Most preferably, the pressure sensor 36 is located so that it underlies the wearer's fifth metatarsal head. The sensors convert mechanical energy into electrical energy. For example, electrostrictive (or synonymously, electroactive) polymers or piezoelectric elements are suitable sensor materials. Sensor 36 preferably has substantially the same material properties as the sole, so as to be substantially undetectable.

Electrostrictive polymers generate energy. When a wearer takes a step, the electrostrictive polymer sensor is flexed and a voltage is generated by the polymer. Suitable electrostrictive polymers include those disclosed in U.S. Pat. No. 6,433,465, which is incorporated herein by reference in its entirety. Other suitable electrostrictive polymers have been tested and developed by SRI International (Stanford, Calif.). Other electrostrictive materials include ceramics available from Applied Ceramics, Inc. (Fremont, Calif.).

Preferred electrostrictive polymers should have high strain rate for comfort and maximum deflection. SRI has developed a process whereby electrodes expand and contract with the polymer, thus greatly enhancing their durability and the controllability of the polymer's response to a given voltage input electrostatic polymer transducer films that can expand or contract in the in-plane directions in response to applied electric fields or mechanical stresses. These transducer films have produced strains up to 100% and pressure up to 100 psi or higher. Preferred electrostrictive polymers include silicones and acrylic elastomers; however, all insulating polymers possess some electrostrictive response. Suitable electrostrictive polymers include, but are not limited to, Hylomar HS3 silicone, NuSil CF19-2186 silicone, 3M VHB 4910 acrylic, Deerfield polyurethane PT6100S, Dow Corning Sylgard 186 silicone, Dow Corning fluorosilicone 730, LaurentL 143HC fluoro-elastomer, Aldrich polybutadiene (PBD) and isoprene natural rubber latex, among others. These and other suitable materials are discussed in "Electrostrictive Polymer Artificial Muscle Actuators", by R. Kombuth, R. Pelrine, J. Eckerle and J. Joseph (unknown publication date)(available at www.erg.sri.com/publications/7247-pa-98-032.pdf), "Artificial Muscle for Small Robots," by R. Pelrine, R. Kombluth, J. Joseph, and S. Chiba (unknown publication date)(available at www.erg.sri.com/publications/10673-PA-00-087.pdf) and "Artificial Muscle Actuators for Exoskeletons," by R. Kombluth, R. Pelrine, S. Shastri, R. Full, and K. Meijer (unknown publication date) (available at www.erg.sri.com/publications/433-PA-00-013.pdf). These references are incorporated herein by reference in their entireties.

Piezoelectric elements also generate a pulse of electrical energy each time the wearer's foot applies a force on the element when impacting the ground. Piezoelectric elements are widely used and commercially available. The electrical pulse, voltage or energy generated by sensor 36 is transmitted to controller 38 via wire 40.

Figure 11:
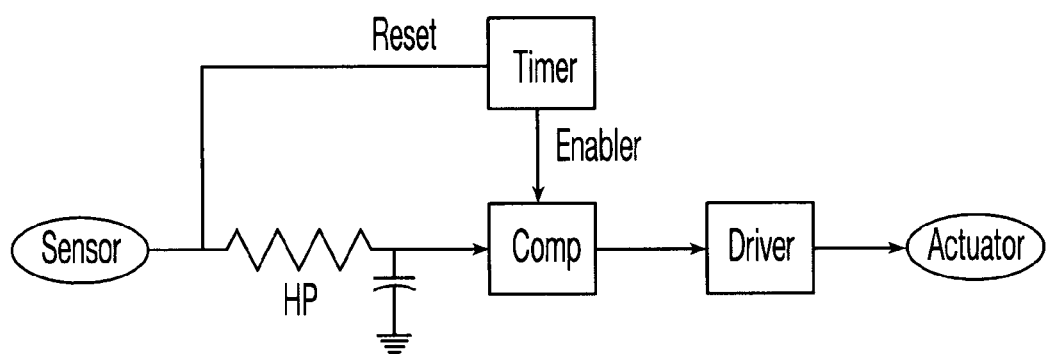
FIG. 11 is a schematic view of a suitable controller usable with the present invention.

Referring again to FIG. 2, the controller 38 is located so that it underlies the heel of a wearer's foot. More preferably, the controller 38 is located in a heel section 34 of the sole assembly within a chamber (not shown) therein. In a preferred embodiment, the controller 38 functions as a simple central processing unit and includes conditioning circuits, such as high-pass filter circuitry followed by magnitude comparator circuitry. The controller 38 may further include a timer. The controller circuitry may be retained on a circuit board having an area as small as about 12 cm². An example of a suitable and commercially available controller is illustrated in FIG. 11, which shows an input signal being split, with one path going through a high pass filter (HP) and the other path through a timer and an enabler before being combined at a comparator. The output of the comparator is fed to an electrical driver and then to a sensor. The electrical driver preferably is a high voltage, high frequency device suitably adapted to be used with piezoelectric sensors. The controller may be located away from the sole, e.g., in upper 12.

Figure 6:
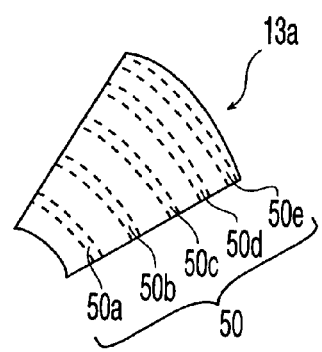
FIG. 6 is a perspective view showing an active-response element in the tongue of the upper.
Figure 7:
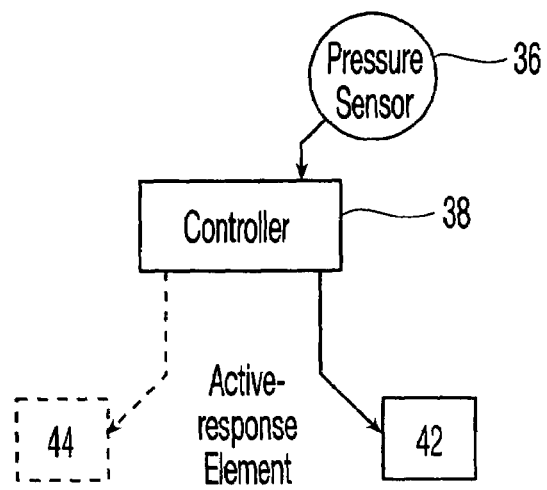
FIG. 7 is a schematic representation of the relationship between the sensor(s), the controller, and active-response elements of FIG. 2.

Referring to FIG. 7, shoe 10 further includes at least one active-response element 42. An additional active-response element 44 is illustrated in phantom. Referring to FIGS. 1-2 and 4-6, suitable active-response elements 42 and 44 include one or more sole stiffener or adjuster 46, a lateral upper stiffener or adjuster 48, a tongue upper adjuster 50, and a lace tightening device or adjuster 51.

Referring to FIG. 2, the sole adjuster 46 in the present embodiment preferably comprises a plurality of aligned piezoelectric fibers, which are electrically connected to the controller 38 via wire 52. Preferably, sole adjuster 46 is positioned diagonally on the sole, and more preferably another sole adjuster is provided and positioned in a diagonal orientation. As illustrated in FIG. 2, sole adjuster 46 comprises two sets of piezoelectric fibers aligning in opposite diagonal directions. Suitable piezoelectric fibers include piezoelectric ceramic fibers manufactured by Advanced Composites of New Jersey. Sole adjusters 46 are configured to resist torsion and flexion as they are arranged diagonally. The longitudinal component of the diagonal orientation resists flexion, and the transverse component resists torsion.

In the present embodiment, the lateral upper adjuster 48 comprises a pad of piezoelectric material coupled to the upper 12. The lateral upper adjuster 48 is electrically connected to the controller 38 via wire 53. The lateral upper adjuster 48 is shown in phantom in FIG. 1 to represent that the lateral upper adjuster is typically not on the exterior of the upper 12. The lateral upper adjuster 48 can be disposed on the exterior or interior surface of the upper 12 or may be disposed between layers of the upper 12. Alternatively, the lateral upper adjuster may be an exoskeleton or an open mesh on the lateral side of the upper, and is either embedded therein or on the surface thereof. When activated, sole adjuster 46 and upper adjuster 48 deformed out-of-plane to provide more stability to the sole and the upper, respectively.

Referring to FIG. 6, the tongue upper adjuster 50 includes a plurality of bands 50*a-e* formed of an electrostrictive polymer sandwiched between the layers of the tongue 13*a*. These bands 50*a-e* are electrically connected to the controller 38 via conductive wire (not shown). The configuration and number of the bands 50*a-e* may be modified, and the present invention is not limited to the illustration in FIG. 6. The length and cross-sectional area of the bands 50*a-e* are determined by the desired force generated by their activation.

Figure 4:
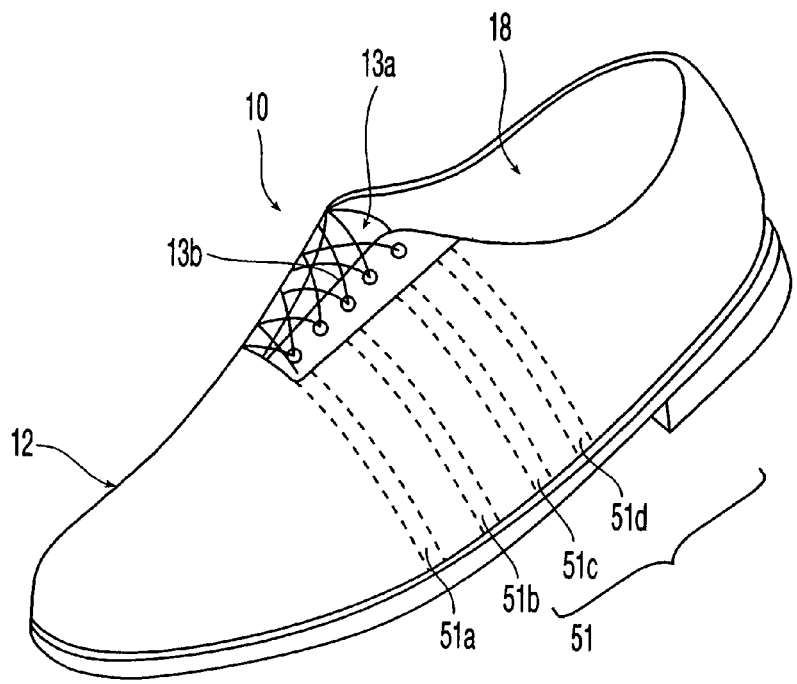
FIG. 4 is a lateral side, perspective view of the golf shoe of FIG. 1 showing an active-response element in the upper, wherein another active-response element has been omitted for clarity.
Figure 5:
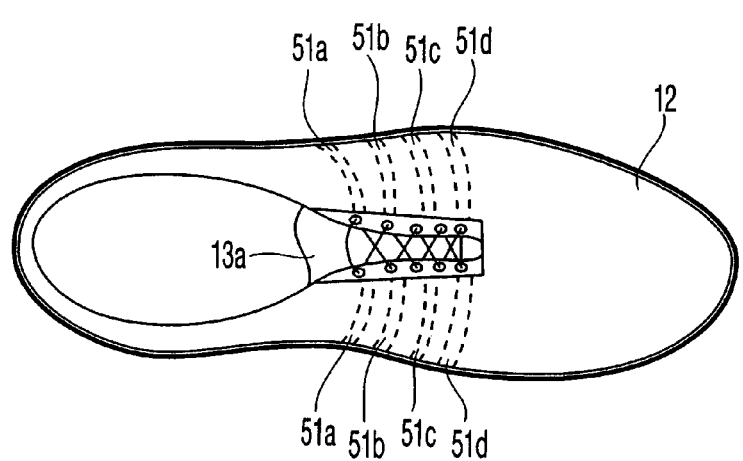
FIG. 5 is a top plan view of the shoe of FIG. 4 showing the active-response element in the upper.

Referring to FIGS. 4 and 5, lace adjuster 51 in the present embodiment in the saddle portion of shoe 10 comprises a plurality of bands 51*a-d* formed of an electrostrictive polymer sandwiched between the layers of the upper 12. Bands 51*a-d* are operatively associated with the laces 13*b* so that movement of the bands 51*a-d* changes the tension in the laces 13*b*. These bands 51*a-d* are also electrically connected to the controller 38 via conductive wire (not shown). The configuration and number of the bands 51*a-d* may be modified, and the present invention is not limited to the illustration in FIGS. 4 and 5. For example, bands 51*a-d* (as well as bands 50*a-e*) can be replaced by a simple broad piece of electrostrictive polymer. The length and cross-sectional area of the bands 50*a-d* are determined by the desired force generated by their activation. For example, if a force of 30-50 Newtons is necessary for maximum tightening, the dimensions of the band may be 3 cm long and 70 mm in cross-sectional area. When activated, tongue upper adjuster 50 expands out of plane (or buckles) while lace adjuster 51 in the saddle contracts to tighten shoe 10.

An aspect of the present invention is to distinguish between a walking movement and a swinging movement. When a golfer is walking, there typically is one step in a short time interval of about 2 seconds. This time interval is defined as a harvesting time interval. The harvesting time interval can be less than about 2 seconds, and can be between about 1 to 2 seconds.

A golfer typically assumes a stance pause before swinging. In addition, when a golfer is swinging, the golfer's movement is quick and forceful. Placement of pressure sensor 36 (see FIG. 2) beneath the head of the wearer's fifth metatarsal head reliably measures rapid pressure changes associated with a golf swing according to empirical testing.

Figure 8:
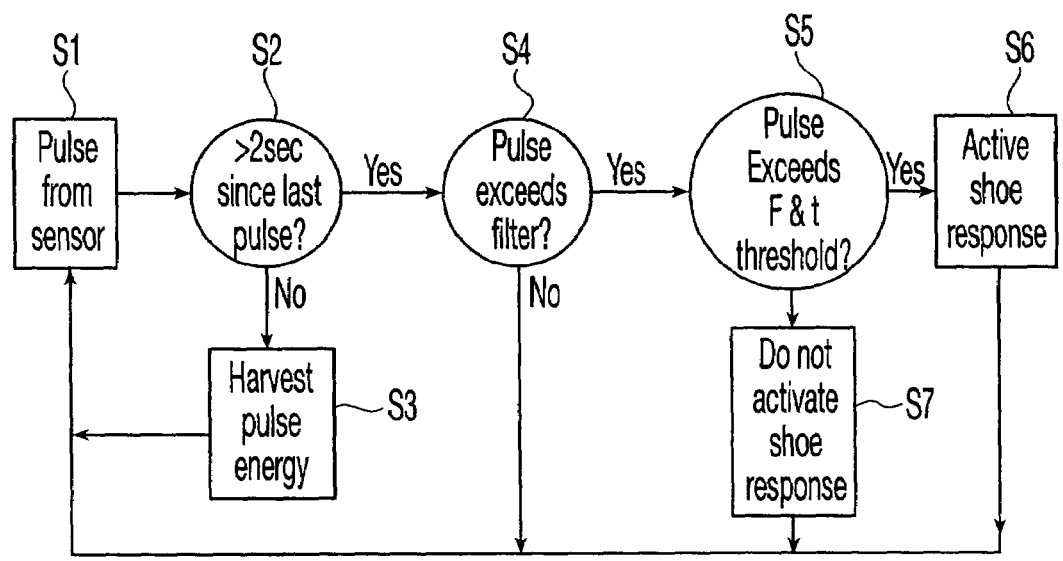
FIG. 8 is a flowchart illustrating the operation of the sensor(s), controller, and the active-response elements.

Referring to FIG. 8, during use a wearer will insert their foot into the chamber 16 (as shown in FIG. 1) and tighten the laces 13b so that the shoe is comfortable for walking. As the wearer is walking, each time the wearer's foot strikes the ground, sensor 36 (see FIG. 2) sends a pulse along wire 40 to the controller 38 (Step S1). In step 2, the controller 38 determines whether a pulse is received within the harvesting time interval. If the pulses are received within the harvesting time interval, the controller 38 recognizes that the wearer is walking and the shoe is in a harvesting mode. In the harvesting mode, energy in the pulses from the sensor 36 is harvested (Step S3) or used to power the controller 38. In addition, in the harvesting mode, the active-response elements 42 and 44 (see FIG. 7) are not activated. The operation returns to step S1 and the sensor 36 senses the next pulse. Some of the harvested energy may be stored in capacitors and/or diodes for use by the controller 38, when harvesting is not occurring. Alternatively, a battery is provided to power controller 38 and the active-response components.

If the pulses are not received within the harvesting time interval, the controller 38 recognizes that the wearer is not walking and the shoe changes to a pre-strike mode. In the pre-strike mode, energy in the pulses from the sensor 36 is not harvested. While the harvesting is not operational, the controller 38 may be powered by stored power or by batteries.

Next in step S4, the controller 38 converts the received pulse magnitude into a frequency. This frequency is compared to a preset filter frequency. In one embodiment, the preferred preset filter frequency is about 10 Hz. More preferably, the preset filter frequency is between about 2 Hz and about 10 Hz. If the sensed frequency is less than the preset filter frequency, the operation returns to step S1 and sensor 36 waits to sense the next pulse, and the active-response elements 42 and 44 (see FIG. 7) are not activated. In this way, the controller 38 is programmed to ignore small spikes in force that are not indicative of a swing. If the sensed frequency is greater than the preset filter frequency, the operation continues to step S5.

In step S5, the controller 38 compares the sensed pulse magnitude to the previously sensed pulse magnitude to determine a magnitude change over a time interval between the pulses. In one embodiment, a preset swing threshold magnitude is about 100 kPa for an average size golfer who has a mass of about 75 kg. More preferably, the swing threshold value is between about 70 kPa and about 140 kPa or higher for golfers having mass between 35 kg and 160 kg, respectively. In one embodiment, the preset, preferred time interval threshold for determining the magnitude change is about 0.5 second or less.

If the magnitude change is greater than the preset swing threshold value and the time interval is less than the preset time interval threshold, the controller 38 recognizes that a swing is occurring, since a swing is characterized by an increase in pressure over a short time interval. As a result, the controller 38 sends an output current via the connecting wires to activate the sole adjuster 46, lateral upper adjuster 48, tongue upper adjuster 50 and lace adjuster 51 active response elements.

This output current causes the sole adjuster 46 to deform out of plane or to buckle and in effect increasing the stability of outsole 32 for the swing, and causes the lateral upper adjuster 48 to do the same. This output current also causes the bands 50a-e of the tongue adjuster 50 to buckle, and causes the lace adjuster bands 51a-d to contract tightening the laces 13b and consequently the upper 12. As a result, the sole assembly 14 and the upper 12 will be more stable during the swing and resist the movement of the wearer's foot relative to the outsole. The active-response elements are very responsive and their activation is initiated and completed when the downswing is initiated, so that the shoe exhibits the characteristics of the stable hitting-platform before the golfer's forward swing. The morphing process to the stable platform takes about 10 milliseconds to about 0.1 second. After this, the operation returns to step S1 and sensor 36 waits to sense the next pulse. The adjusters automatically relax in about 5 seconds when no output from the driver is received by the sensor (see FIG. 11). The stored energy is sufficient for several swings to account for practice swings, if there is no significant pause between the practice swing(s) and the actual swing. Once there is a pause, the shoes will be ready to tighten for a golf swing and will remain so until the sensor detects steps. The shoes would activate if the practice swings are quick enough or close enough to an actual swing.

If the magnitude change is less than the preset swing threshold value and/or the time interval is more than the preset time interval threshold, the controller 38 recognizes that a swing is not occurring. As a result, the controller 38 does not send an output signal to the active-response elements and the active-response elements do not change. Consequently, the shoe characteristics do not change and remain that of the soft/flexible walking-platform. The operation returns to step S1 and sensor 36 waits to sense the next pulse.

In order for the active-response elements to be triggered, a movement must be characterized as a swing, which occurs if the magnitude and time interval thresholds are met, as illustrated in step S5. Typically, a swing is not characterized by an increase in pressure over a long time, and a swing is not characterized by a maintained pressure over a short time.

According to the above description, if the golfer is walking and takes a pause to watch another golfer take a shot, the controller 38 will only signal the active-response elements if the first step after the pause is taken rapidly and with sufficient force to meet the magnitude and time interval thresholds, i.e., almost as if the golfer were starting to run. If these conditions are met, the shoe characteristics would change to the stable hitting platform for rapid step. This is acceptable, since support would be useful during a fast running movement.

Also according to the above description, if the golfer is walking and takes a pause to watch another golfer take a shot, and the golfer then takes a slow or soft swing such as greenside play, the controller will not signal the active-response elements. In this case, the shoe characteristics would be those of the soft/flexible walking platform. This is acceptable, since a high degree of stability is not necessary for a soft swing or for putting.

Figure 9:
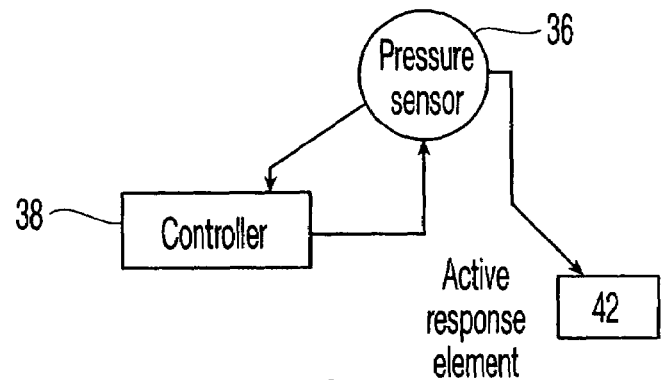
FIG. 9 is a schematic representation of an alternative relationship between the sensor(s), the controller and the active-response element.

With reference to FIG. 9 in an alternative embodiment, the outsole includes pressure sensor 36, controller 38 and active-response element 42. In this embodiment, the pressure sensor 36 sends a pulse to the controller 38. When the controller 38 determines that a swing is occurring using the previously discussed thresholds, the controller 38 sends an output signal back to the pressure sensor 36. The sensor 36 sends a signal to the active-response element 42 that activates the active-response element 42. In this embodiment, the sensor 36 acts as a sensor and an actuator. Having sensor 36 act as an actuator reduces the cost of the system.

Figure 10:
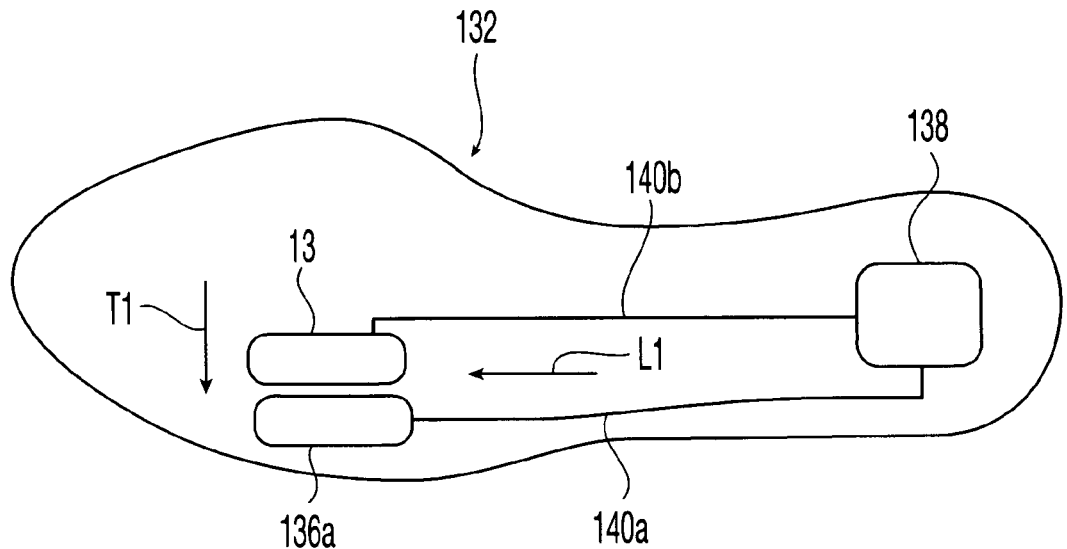
FIG. 10 is a schematic, top plan view of another preferred embodiment of the present invention including various sensors and a controller within an outsole.

FIG. 10 refers to another embodiment of an outsole 132 with a plurality of sensors 136a and 136b and a controller 138. The sensors 136a, b are electrically connected to the controller 138 via wires 140a, b, respectively. Preferably, the sensors 136a, b are inversely wired to effect a common mode rejection strategy. When the golfer walks, the foot motion is along the longitudinal direction L and both sensors would experience pressure peak at substantially the same time. When the golfer swings, the foot motion aligns with transverse direction T, and the sensors would experience pressure peak at different times.

Preferably, the pressure sensors 136a, b are located so that they underlie the ball of a wearer's foot. More preferably, the pressure sensors 136a, b are located so that they underlie the lateral side of the ball of the wearer's foot. Most preferably, the pressure sensor 136a is located so that it underlies the head of the wearer's fifth metatarsal head and the pressure sensor 136b is located so that it underlies the head of the wearer's fourth metatarsal head. It is desirable that the pressure sensor 136b is spaced transversely and medially from the pressure sensor 136a. Generally, sensors 136a and 136b can be positioned under any two metatarsal heads, so long as the sensors are spaced apart transversely from each other. The sensors used for sensor 36 may also be used for pressure sensors 136a, b.

As the wearer walks, each time the wearer's foot strikes the ground, each sensor 136a, b (see FIG. 7) sends a pulse along wires 140a, b to the controller 138. During walking, the controller 138 would compare the two pressure values from each sensor 136a, b. If the two pressures are similar within a predetermined pressure threshold, the pulses would cancel each other out. As a result, the controller 138 would recognize that the wearer is walking. Walking is a movement in a longitudinal direction illustrated by arrow L1. The controller 138 would not send an output signal to the active-response elements previously discussed. Consequently, the active-response elements are not activated. The sensors 136a, b would continue to sense the movements of the wearer and the energy generated is harvested as described above.

During swinging, the controller 138 would compare the two pressure values from each of the sensors 136a, b. Swinging is a movement in a transverse or lateral direction illustrated by arrow T1. When a golfer walks, the movement along line L1 would cause both sensors to sense pressure at about the same time. Since they are wired inversely as discussed above, no signal is transmitted to the controller. When a golfer swings, the movement along line T1 causes one sensor to sense pressure before the other sensor. This time shift prevents the signals from canceling each other, and the controller would recognize two distinct pressure signals and know that the golfer is swinging. The controller 138 would then send an output signal to the active-response elements, such as those described above, to change the shoe characteristics from the soft/flexible walking platform to the stable hitting platform. Afterward, the active response elements relax and the sensors 136a, b would then continue to sense the movements of the wearer.

While various descriptions of the present invention are described above, it is understood that the various features of the embodiments of the present invention shown herein can be used singly or in combination thereof. For example, the multi-lobed of the present invention can be incorporated in any spherical objects in flight. This invention is also not to be limited to the specifically preferred embodiments depicted therein.

What is claimed is:

1. A shoe comprising:
   an upper, at least one active-response element, a sole coupled to the upper to define a chamber for receiving a wearer's foot, at least one sensor, and a controller operatively connected to said sensor and said active-response element,
   wherein said controller determines whether the wearer is walking or swinging and when the wearer is swinging, said controller sends an output current to said active-response element and said active-response element changes said shoe from an initial state where the shoe exhibits a first set of characteristics to a transitory state where the shoe exhibits a second set of characteristics different from said first set of characteristics.

2. The shoe of claim 1, wherein said output current is sent to said sensor, and said sensor sends said output current to said active-response element.

3. The shoe of claim 1, wherein said active-response element comprises a sole adjuster, an upper adjuster, a tongue adjuster or a lace adjuster.

4. The shoe of claim 1, wherein said controller sends said output current if said sensor senses a pressure greater than a preset swing threshold within a preset time interval threshold.

5. The shoe of claim 1, wherein said sensor is a pressure sensor that underlies the ball of the wearer's foot.

6. The shoe of claim 5, wherein the pressure sensor underlies the wearer's foot's fifth metatarsal head.

7. The shoe of claim 4, wherein the swing threshold is between about 70 kPa to about 140 kPa.

8. The shoe of claim 7, wherein the swing threshold is about 100 kPa.

9. The shoe of claim 4, wherein the time interval threshold is about 0.5 second.

10. The shoe of claim 7, wherein the time interval threshold is about 0.5 second.

11. The shoe of claim 1, wherein the first set of characteristics is indicative of walking.

12. The shoe of claim 11, wherein the second set of characteristics is indicative of swinging.

13. The shoe of claim 12, wherein during walking said sensor generates energy that is harvested.

14. The shoe of claim 12, wherein during swinging the controller converts the harvested energy to said output current.

15. The shoe of claim 1, wherein the shoe is more stable when exhibiting the second set of characteristics than the first set of characteristics.

16. The shoe of claim 15, when exhibiting the second set of characteristics the wearer's foot is less movable relative to the shoe.

17. The shoe of claim 1, wherein the sole comprises at least two sensors, wherein the two sensors are located proximately under any two metatarsal heads.

18. The shoe of claim 17, wherein the two sensors are spaced apart.

19. The shoe of claim 17, wherein one sensor is located under the fourth metatarsal bone and another sensor is located under the fifth metatarsal bone.

20. The shoe of claim 17, wherein when the wearer is walking the at least two sensors sense pressure peaks at about the same time.

21. The shoe of claim 17, wherein when the wearer is swinging the at least two sensors sense pressure peaks sequentially.

22. The shoe of claim 1, wherein the at least one sensor is made of piezoelectric material.

23. The shoe of claim 1, wherein the at least one sensor is made of an insulating polymer.

24. The shoe of claim 23, wherein the at least one sensor is made of a silicone or an acrylic elastomer.

25. The shoe of claim 23, wherein the at least one sensor is made of polyurethane, fluorosilicone, fluoro-elastomer, polybutadiene or isoprene.

26. The shoe of claim 3, wherein the sole adjuster is positioned diagonally relative to the sole.

27. The shoe of claim 3, wherein the sole adjuster comprises two adjusters positioned diagonally relative to the sole and diagonally opposite from each other.

28. A shoe comprising an upper and a sole coupled to the upper to define a chamber for receiving a wearer's foot, wherein said shoe distinguishes whether the wearer is walking or swinging.

* * * * *